(12) United States Patent
Biggadike et al.

(10) Patent No.: US 7,291,609 B2
(45) Date of Patent: *Nov. 6, 2007

(54) SPECIFIC GLUCOCORTICOSTEROID COMPOUND HAVING ANTI-INFLAMMATORY ACTIVITY

(75) Inventors: Keith Biggadike, Stevenage (GB); Deborah Needham, Stevenage (GB)

(73) Assignee: Glaxo Group Limited, Greenford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 10/564,299

(22) PCT Filed: Jul. 9, 2004

(86) PCT No.: PCT/EP2004/007820

§ 371 (c)(1),
(2), (4) Date: Sep. 12, 2006

(87) PCT Pub. No.: WO2005/005452

PCT Pub. Date: Jan. 20, 2005

(65) Prior Publication Data

US 2007/0043007 A1    Feb. 22, 2007

(30) Foreign Application Priority Data

Jul. 11, 2003   (GB)   .................... 0316290.6

(51) Int. Cl.
A61K 31/56   (2006.01)
C07J 3/00   (2006.01)

(52) U.S. Cl. .................... 514/179; 514/180; 552/610
(58) Field of Classification Search ................ 514/179, 514/180; 552/610
See application file for complete search history.

(56) References Cited

U.S. PATENT DOCUMENTS

| | | | |
|---|---|---|---|
| 3,856,828 A | 12/1974 | Phillipps et al. |
| 5,552,438 A | 9/1996 | Christensen, IV |
| 6,172,054 B1 | 1/2001 | Clark |
| 6,245,804 B1 | 6/2001 | Lehmann et al. |
| 6,395,738 B1 | 5/2002 | Ohshima et al. |
| 6,897,224 B2 | 5/2005 | Jaroch et al. |

FOREIGN PATENT DOCUMENTS

| | | |
|---|---|---|
| GB | 1384372 | 2/1975 |
| GB | 1514476 | 6/1978 |
| GB | 2079755 | 1/1982 |
| GB | 2137206 | 10/1984 |
| WO | WO 89/03390 | 4/1989 |
| WO | WO 93/13055 | 7/1993 |
| WO | WO 95/34534 | 12/1995 |
| WO | WO 97/41867 | 11/1997 |
| WO | WO 98/30537 | 7/1998 |
| WO | WO 98/54159 | 12/1998 |
| WO | WO 99/16766 | 4/1999 |
| WO | WO 99/32127 | 7/1999 |
| WO | WO 99/47505 | 9/1999 |
| WO | WO 99/62875 | 12/1999 |
| WO | WO 00/66590 | 11/2000 |
| WO | WO 01/04118 | 1/2001 |
| WO | WO 01/10143 | 2/2001 |
| WO | WO 01/16128 | 3/2001 |
| WO | WO 01/42193 | 6/2001 |
| WO | WO 02/00679 | 1/2002 |
| WO | WO 02/02565 | 1/2002 |
| WO | WO 02/26722 | 4/2002 |
| WO | WO 02/40030 | 5/2002 |
| WO | WO 02/50021 | 6/2002 |
| WO | WO 02/066422 | 8/2002 |
| WO | WO 02/070490 | 9/2002 |
| WO | WO 02/076933 | 10/2002 |
| WO | WO 03/008277 | 1/2003 |
| WO | WO 03/024439 | 3/2003 |
| WO | WO 03/042160 | 5/2003 |

(Continued)

OTHER PUBLICATIONS

Austin et al., "*Mometasone furoate* is a less specific glucocorticoid than fluticasone propionate," *Eur Resp J.* 20(6):1386-1392 (Dec. 2002).

(Continued)

*Primary Examiner*—Barbara P. Badio
(74) *Attorney, Agent, or Firm*—James P. Riek

(57) ABSTRACT

A compound of formula (I):

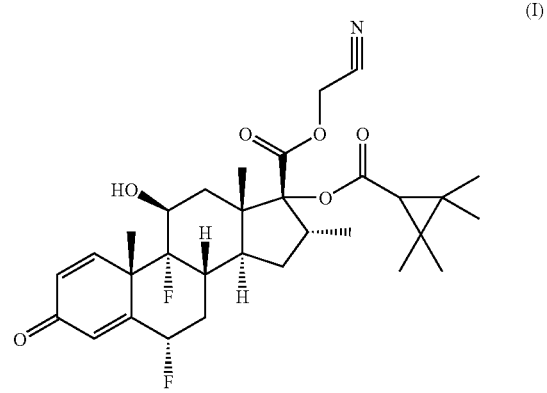

or a physiologically acceptable solvate thereof.

6 Claims, No Drawings

FOREIGN PATENT DOCUMENTS

| | | |
|---|---|---|
| WO | WO 03/059899 | 7/2003 |
| WO | WO 03/061651 | 7/2003 |
| WO | WO 03/072539 | 9/2003 |
| WO | WO 03/082280 | 10/2003 |
| WO | WO 03/082787 | 10/2003 |
| WO | WO 03/082827 | 10/2003 |
| WO | WO 03/086294 | 10/2003 |
| WO | WO 03/101932 | 12/2003 |
| WO | WO 03/104195 | 12/2003 |
| WO | WO 2004/005229 | 1/2004 |
| WO | WO 2004/009016 | 1/2004 |
| WO | WO 2004/009017 | 1/2004 |
| WO | WO 2004/016578 | 2/2004 |
| WO | WO 2004/018429 | 3/2004 |
| WO | WO 2004/022547 | 3/2004 |
| WO | WO 2004/024728 | 3/2004 |
| WO | WO 2004/026248 | 4/2004 |
| WO | WO 2004/037768 | 5/2004 |
| WO | WO 2004/037773 | 5/2004 |
| WO | WO 2004/037807 | 5/2004 |
| WO | WO 2004/039762 | 5/2004 |
| WO | WO 2004/039766 | 5/2004 |
| WO | WO 2004/056823 | 7/2004 |
| WO | WO 2004/103998 | 12/2004 |
| WO | WO 03/091204 | 11/2006 |

OTHER PUBLICATIONS

Fuji et al., "Novel phosphodiesterase 4 inhibitor T-440 reverses and prevents human bronchial contraction induced by allergen," *J Pharmacol Exp Ther* 284(1):162 (1998).

Landells et al., "Oral administration of the phosphodiesterase (PDE)4 inhibitor, V11294A inhibits ex-vivo agonis-induced-cell activation," *Eur Resp J (/annu Cong Eur Resp Soc. Geneva)* 12(Suppl. 28) Abst P2393 (Sep. 1998).

Rachwal et al., "Chemistry of loteprednol crabonate and related steriods. II. Reactions at ring C and NMR structural studies of the resulting compounds," *Steroids* 63 (4):193-201 (1998).

Ray et al., "Induction of the E-selectin promoter by interleukin 1 and tumour necrosis factor $\chi$, and inhibition by glucocorticoids," *Biochem J.* 328:707-715 (Dec. 1997).

Phillips, GH et al., "Synthesis and structure activity Relationships in a series of Anti-inflammatory Corticosteroid Analogues, Halomethyl Androstane—17B-carbothioates and -17B-carboselenoates," Journal of Medicinal Chemistry 1994, 37, 3717-3729.

Ueno et al., "Synthesis and evaluation of anti-inflammatory activities of a series of corticosteroid 17.alpha.-esters containing a functional group," *Journal of Medicinal Chemistry* 34(8):2468-2471 (Aug. 1991).

SPECIFIC GLUCOCORTICOSTEROID COMPOUND HAVING ANTI-INFLAMMATORY ACTIVITY

CROSS-REFERENCE TO RELATED APPLICATIONS

This application is filed pursuant to 35 U.S.C. § 371 as a United States National Phase Application of International Application No. PCT/EP2004/007820 filed 9 Jul. 2004, which claims priority from GB 0316290.6 filed 11 Jul. 2003.

FIELD OF THE INVENTION

The present invention relates to a compound which is a glucocorticoid receptor agonist of the androstane series. The present invention also relates to pharmaceutical formulations containing the compound and to therapeutic uses thereof, particularly for the treatment of inflammatory and allergic conditions.

BACKGROUND OF THE INVENTION

Glucocorticosteroids which have anti-inflammatory properties are known and are widely used for the treatment of inflammatory disorders or diseases such as asthma and rhinitis. However, we have identified a novel glucocorticosteroid.

SUMMARY OF THE INVENTION

Thus, according to one aspect of the invention, there is provided a compound of formula (I)

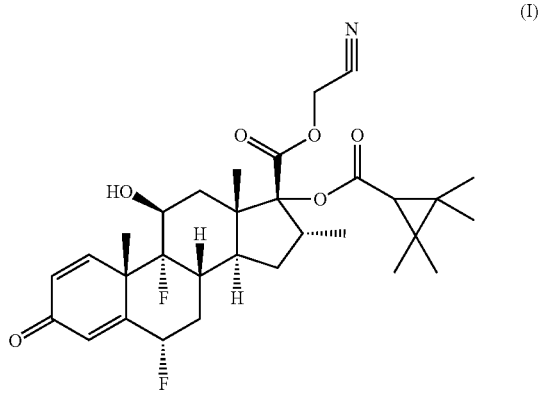

(I)

or a physiologically acceptable solvate thereof.

Examples of solvates include hydrates.

References hereinafter to the compound according to the invention includes both compound of formula (I) and solvates thereof.

It will be appreciated that the invention includes within its scope all stereoisomers of the compound of formula (I) and mixtures thereof.

Preferably, the absolute stereochemistry will be as shown in the representation of compound of formula (I).

The compound of formula (I) is named: 6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester.

The compound of formula (I) has potentially beneficial anti-inflammatory or anti-allergic effects, particularly upon topical administration, demonstrated by, for example, its ability to bind to the glucocorticoid receptor and to illicit a response via that receptor. Hence, the compound of formula (I) is potentially useful in the treatment of inflammatory and/or allergic disorders.

Examples of disease states in which the compound of the invention may have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

The compound of the invention may also have use in the treatment of conjunctiva and conjunctivitis.

It will be appreciated by those skilled in the art that reference herein to treatment extends to prophylaxis as well as the treatment of established conditions.

As mentioned above, the compound of formula (I) may be useful in human or veterinary medicine, in particular as an anti-inflammatory and anti-allergic agent.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or a physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compound according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compound according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 µg-10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 µg-2000 µg, preferably about 20 µg-500 µg of a compound of formula (I). Administration may be once daily or several times daily, for example 2, 3, 4 or 8 times, giving for example 1, 2 or 3 doses each time. The overall daily dose with an aerosol will be within the range 100 µg-10 mg preferably, 200 µg-2000 µg. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compound according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example another corticosteroid or an NSAID), an anticholinergic agent, a $\beta_2$-adrenoreceptor agonist, an anti-infective agent (e.g. an antibiotic or an antiviral), or an antihistamine. Preferred are combinations comprising a compound of formula (I) or a pharmaceutically acceptable salt, solvate or physiologically functional derivative thereof together with a $\beta_2$-adrenoreceptor agonist, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

A combination comprising of compound of the invention together with a $\beta_2$-adrenoreceptor agonist is particularly preferred.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period such as salmeterol or formoterol.

Preferred long acting $\beta_2$-adrenoreceptor agonists include those described in WO 02/066422, WO 02/070490, WO 02/076933, WO 03/024439, WO 03/072539, WO 03/091204, WO 04/016578, WO 04/022547, WO 04/037807, WO 04/037773, WO 04/037768, WO 04/039762, WO 04/039766, WO 01/42193 and WO 03/042160.

Especially preferred long-acting $\beta_2$-adrenoreceptor agonists include compounds of formula (XX):

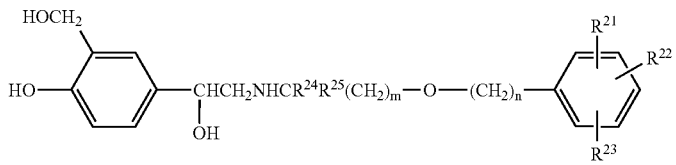

(XX)

or a salt or solvate thereof, wherein:
m is an integer of from 2 to 8;
n is an integer of from 3 to 11,
with the proviso that m+n is 5 to 19,
$R^{21}$ is —$XSO_2NR^{26}R^{27}$ wherein X is —$(CH_2)_p$— or $C_{2-6}$ alkenylene;
$R^{26}$ and $R^{27}$ are independently selected from hydrogen, $C_{1-6}$alkyl, $C_{3-7}$cycloalkyl, $C(O)NR^{28}R^{29}$, phenyl, and phenyl($C_{1-4}$alkyl)-, or $R^{26}$ and $R^{27}$, together with the nitrogen to which they are bonded, form a 5-, 6-, or 7-membered nitrogen containing ring, and $R^{26}$ and $R^{27}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{28}$, —$SO_2NR^{28}R^{29}$, —$CONR^{28}R^{29}$, —$NR^{28}C(O)R^{29}$, or a 5-, 6- or 7-membered heterocyclic ring;
$R^{28}$ and $R^{29}$ are independently selected from hydrogen, $C_{1-6}$alkyl, $C_{3-6}$cycloalkyl, phenyl, and phenyl($C_{1-4}$alkyl)-; and
p is an integer of from 0 to 6, preferably from 0 to 4;
$R^{22}$ and $R^{23}$ are independently selected from hydrogen, $C_{1-6}$alkyl, $C_{1-6}$-alkoxy, halo, phenyl, and $C_{1-6}$haloalkyl; and
$R^{24}$ and $R^{25}$ are independently selected from hydrogen and $C_{1-4}$alkyl with the proviso that the total number of carbon atoms in $R^{24}$ and $R^{25}$ is not more than 4.

Especially preferred long-acting $\beta_2$-adrenoreceptor agonists are:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyeth}-2-(hydroxymethyl) phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]foramide, and
N-2{2-[4-(3-phenyl-4-methoxyphenyl)aminophenyl] ethyl}-2-hydroxy-2-(8-hydroxy-2(1H)-quinolinon-5-yl) ethylamine.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro -11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (eg. the 17-propionate ester or the 17,21-dipropionate ester), budesonide, flunisolide, mometasone esters (eg. the furoate ester), triamcinolone acetonide, rofleponide, ciclesonide (16α, 17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may posess selectivity for transrepression over transactivation and that may be useful in combination therapy include those covered in the following patents: WO03/082827, WO01/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS inhibitors, tryptase and elastase inhibitors, beta-2 integrin antagonists and adenosine receptor agonists or antagonists (e.g. adenosine 2a agonists), cytokine antagonists (e.g. chemokine antagonists, such as a CCR3 antagonist) or inhibitors of cytokine synthesis, or 5-lipoxygenase inhibitors. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Of particular interest is use of the compound of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as Cl-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropyl-benzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Suitable anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (e.g. as the bromide, CAS 22254-24-6, sold under the name Atrovent), oxitropium (e.g. as the bromide, CAS 30286-75-0) and tiotropium (e.g. as the bromide, CAS 136310-93-5, sold under the name Spiriva). Also of interest are revatropate (e.g. as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (e.g. as the bromide, CAS 26095-59-0, sold under the name Spasmomen), trospium chloride (CAS 10405-$O_2$-4) and solifenacin (CAS 242478-37-1, or CAS 242478-38-2 for the succinate also known as YM-905 and sold under the name Vesicare).

Other suitable anticholinergic agents include compounds of formula (XXI), which are disclosed in U.S. patent application 60/487,981:

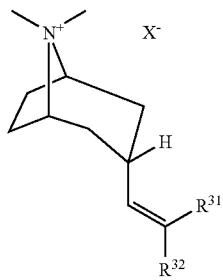

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not In excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in US patent application 60/511,009:

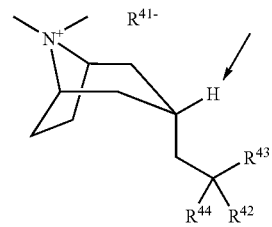

(XXII)

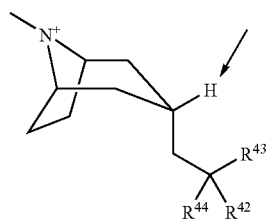

(XXIII)

wherein:
the H atom indicated is in the exo position;
$R^{41}$ represents an anion associated with the positive charge of the N atom. $R^{41}$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl(having 6 to 10 carbon atoms), heterocycloalkyl(having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, $—OR^{45}$, $—CH_2OR^{45}$, $—CH_2OH$, $—CN$, $—CF_3$, $—CH_2O(CO)R^{46}$, $—CO_2R^{47}$, $—CH_2NH_2$, $—CH_2N(R^{47})SO_2R^{45}$, $—SO_2N(R^{47})(R^{48})$, $—CON(R^{47})(R^{48})$, $—CH_2N(R^{48})CO(R^{46})$, $—CH_2N(R^{48})SO_2(R^{46})$, $—CH_2N(R^{48})CO_2(R^{45})$, $—CH_2N(R^{48})CONH(R^{47})$;
$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;
$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;
$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $C_1-C_6)$alkyl$(C_3-C_7)$heterocycloalkyl, $(C_1-C_6)$alkyl-aryl, and $(C_1-C_6)$alkyl-heteroaryl, including, for example:
(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, e.g diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine and cetirizine.

Examples of preferred anti-histamines include loratidine, desloratidine, fexofenadine and cetirizine.

The invention thus provides, in a further aspect, a combination comprising a compound of formula (I) a pharmaceutically acceptable solvate or physiologically functional derivative thereof together with a PDE4 inhibitor.

The invention thus provides, in a further aspect, a combination comprising a compound of formula (I) a pharmaceutically acceptable solvate or physiologically functional derivative thereof together with a $\beta_2$-adrenorecptor agonist.

The invention thus provides, in a further aspect, a combination comprising a compound of formula (I) a pharmaceutically acceptable solvate or physiologically functional derivative thereof together with an anticholinergic.

The Invention thus provides, In a further aspect, a combination comprising a compound of formula (I) a pharmaceutically acceptable solvate or physiologically functional derivative thereof together with an antihistamine.

The invention thus provides, in a further aspect, a combination comprising a compound of formula (I) a pharmaceutically acceptable solvate or physiologically functional derivative thereof together with a PDE4 inhibitor and a $\beta_2$-adrenoreceptor agonist.

The invention thus provides, in a further aspect, a combination comprising a compound of formula (I) a pharmaceutically acceptable solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably the individual compounds of such combinations may be administered simultaneously in a combined pharmaceutical combination. Appropriate doses of known therapeutic agents will be readily appreciated by those skilled in the art.

Solvates of the compound of formula (I) which are not physiologically acceptable may be useful as intermediates in the preparation of compounds of formula (I) or physiologically acceptable solvates thereof.

The compound of formula (I) or solvates thereof demonstrates agonism at the glucocorticoid receptor.

The compound of formula (I) or solvates thereof may demonstrate good anti-inflammatory properties, with predictable pharmacokinetic and pharmacodynamic behaviour. It may have an attractive side-effect profile, demonstrated, for example, by increased selectivity for the glucocorticoid receptor over the progesterone receptor and increased selectivity for glucocorticoid receptor mediated transrepression over transactivation and is likely to be compatible with a convenient regime of treatment In human patients.

DETAILED DESCRIPTION

The following non-limiting Examples illustrate the invention:

EXAMPLES

General

Chromatographic purification was performed using prepacked Bond Elut silica gel cartridges available commercially from Varian or by flash chromatography on prepacked Biotage silica columns. These cartridges were pre-conditioned with dichloromethane prior to use. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve). $^1H$ NMR spectra were obtained in $CDCl_3$ on a Bruker DPX 400 spectrometer working at 400.13 MHz and 9.4 Tesla using as internal standard the signal from the residual protonated solvent at 7.25 ppm.

Intermediates

Intermediate 1: 2,3-dimethyl-1-[(2,2,3,3-tetramethylcyclopropyl)carbonyl]-1H-imidazol-3-ium chloride Oxalyl chloride (360 ml, 4.1 mol) was added over 65 min to a stirred solution of 2,2,3,3-tetramethylcyclopropane carboxylic acid (600 g, 4.2 mol) in dichloromethane (3.6 L) at 34° C. The solution was then heated to reflux for 30 min and then cooled to 5° C. A solution of 1,2-dimethylimidazole (490 g, 5.1 mol) in dichloromethane (1.2 L) was added over 45 min maintaining the internal temperature around 5° C. The resulting suspension was then warmed to 18° C. and acetone (4.8 L) was added over 45 minutes maintaining the internal temperature around 18° C. The slurry was cooled to 5° C. over 30 minutes, stirred at 5° C. for 30 minutes and then filtered. The product was collected by filtration, washed with acetone:dichloromethane (3:1, 3×1.2 L), sucked dry and then dried in a vacuum oven at 25-30° C. for 10 hours to give Intermediate 1 as a white solid (890 g) 1H nmr: $\delta_H$($CDCl_3$, 400 MHz) 8.45 (d, J 2.4 Hz, 1 H), 8.11 (d, J=2.4 Hz, 1 H), 4.21 (s, 3 H), 2.96 (s, 3 H), 2.21 (s, 1 H), 1.43 (s, 6 H), 1.33 (s, 6H).

Examples

Example 1

6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester Method A Bromoacetonitrile (0.229 ml, 3.29 mmol) was added to a stirred and cooled (ice) solution of 6α,9α-Difluoro-11β-hydroxy-16α-methyl-3-oxo-17α-(2,2,3,3-tetramethycyclopropylcarbonyl)oxy-androsta-1,4-diene-17-carboxylic acid (prepared as described in WO 2003/3072592) (634 mg, 1.22 mmol) and sodium carbonate (1.29 g, 12.2 mmol) in DMF (15 ml) under nitrogen and the mixture stirred at room temperature for 2 h. More sodium carbonate (258 mg) was added and the mixture stirred for a further 18 h. 2M HCl (20 ml) was added dropwise followed by water (25 ml) and the mixture was extracted with ethyl acetate (2×50 ml). The combined organic extracts were washed successively with aqueous sodium hydrogen carbonate (50 ml) and brine (50 ml) and dried through a hydrophobic frit and evaporated to dryness. Purification on a Bond Elut cartridge using initially cyclohexane and finally cyclohexane:ethyl acetate 3:1 gave the title compound as a white solid (485 mg): LCMS retention time 3.79 min, m/z 560 $MH^+$ Method B 6α,9α-Difluoro-11β,17α-dihydroxy-16α-methyl-3-oxo-androsta-1,4-diene-17β-carbocylic acid (G. H. Phillipps et al., (1994) Journal of Medicinal Chemistry, 37, 3717-3729) (490 g, 1.2 mol) and Intermediate 1 (790 g, 3.1 mol) were suspended in 3-pentanone (7.3 L). To the stirred suspension was added over 10 min a solution of 1,2-dimethylimidazole (120 g, 1.2 mol) in water (730 ml) maintaining the internal temperature around 19° C. After 35 min, 1-methylpiperazine (230 ml, 2.1 mol) was added over 10 min keeping the internal temperature around 19° C. The mixture was stirred for 30 min and then washed sequentially with 2M HCl (290 ml) and water (290 ml). Diisopropylethylamine (430 ml, 2.5 mol) and bromoacetonitrile (120 ml, 1.7 mol) were added sequentially to the solution and the mixture was heated to 53° C. for 13 hours. The solution was cooled to 34° C. and 1-methylpiperazine (105 ml) was added. The mixture was stirred around 34° C. for a further hour, cooled to 25° C. and washed sequentially with 2M HCl (290 ml), water (290 ml), 2% potassium carbonate solution (290 ml) and water (290 ml). The organic solution was concentrated to 3.9 L by atmospheric distillation, cooled to 75° C. and seeded with crystals of Example 1. 2,2,4-Trimethylpentane (6.83 L) was added over 3 hours at 75° C. and the slurry was then cooled to 10° C. over 2 hours, stirred for a further 30 min and then filtered. The product was washed with 3-pentanone:2,2,4-trimethylpentane (1:3, 3×1 L), sucked dry and finally dried in a vacuum oven at 50° C. for 12 hours to give Example 1 as a white solid (640 g) identical to material obtained using Method A.

Pharmacological Activity

Pharmacological activity may be assessed in functional in vitro assays of glucocorticoid agonist activity.

The functional assay based on that described by K. P. Ray et al., Biochem J. (1997), 328, 707-715 provides a measure of transrepressive activity of a glucocorticoid agonist. A549 cells stably transfected with a reporter gene containing the NF-κB responsive elements from the ELAM gene promoter coupled to sPAP (secreted alkaline phosphatase) are treated with test compounds at appropriate doses for 1 hour at 37° C. The cells are then stimulated with tumour necrosis factor (TNF, 10 ng/ml) for 16 hours, at which time the amount of alkaline phosphatase produced is measured by a standard colourimetric assay. Dose response curves are constructed from which $EC_{50}$ values may be estimated.

An $EC_{50}$ value of <0.1 nM was observed for Example 1

The functional assay based on that described by R. J. H. Austin et al., Eur Resp J. (2002), 20, 1386-1392 measures the ability of compounds to directly transactivate gene expression. A549 cells stably transfected with a reporter gene containing the glucocorticoid responsive region of the mouse mammary tumour virus long terminal repeat (MMTV-LTR) coupled to renilla luciferase were treated with test compounds at appropriate doses for 6 hour at 37° C. The amount of luciferase activity present within the cells is then determined by measuring the light emitted following incubation with a suitable substrate. Dose response curves were constructed from which $EC_{50}$ values were estimated and from which maximal responses are calculated relative to Dexamethasone (100%).

Compound of Example 1 showed a maximal response of <5% in this assay.

Assay for Progesterone Receptor Activity

The human breast cancer cell line T47D has been reported to upregulate an endogenous alkaline phosphatase in response to progestins (Di Lorenzo et al., Cancer Research (1991) 51, 4470-4475. T47D cells were seeded into 96 well plates at a density of 1×10⁵ cells per well and grown overnight at 37° C. Steroids were dissolved in DMSO, added to the cells (final DMSO concentration 0.7%), and incubated for 24 hours at 37° C. The cells were then washed with PBS and lysed with RIPA buffer (1% IGEPAL, 0.5% Na deoxycholate, 0.1% SDS in phosphate buffered saline). Alkaline phosphatase activity was measured spectrophotometrically (405 nm) using p-nitrophenylphosphate (1.5 mg/ml) as a substrate dissolved in 1M diethanolamine, 0.28M NaCl, 0.5 mM $MgCl_2$. Dose response curves were constructed from which $EC_{50}$ values were estimated.

The $EC_{50}$ value for compound of Example 1 In this assay was >100 nM.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

What is claimed is:

1. A compound of formula (I):

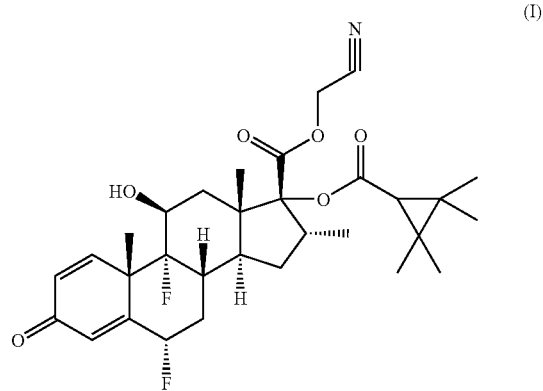

or a physiologically acceptable solvate thereof.

2. A pharmaceutical composition comprising a compound of formula (I) as defined in claim 1 or a physiologically acceptable solvate thereof together, in admixture with one or more physiologically acceptable diluents or carriers.

3. A pharmaceutical aerosol formulation comprising a compound of formula (I) as defined in claim 1 or a physiologically acceptable solvate thereof, and a fluorocarbon or hydrogen-containing chlorofluoro carbon as propellant, optionally in combination with a surfactant and/or a cosolvent.

4. A pharmaceutical composition according to claim 3 which further comprises one or more therapeutically active agents.

5. A pharmaceutical composition according to claim 4 in which said one or more therapeutically active agents is a β$_2$-adrenoreceptor agonist.

6. A method for the treatment of a human or animal subject with an inflammatory and/or allergic condition, which method comprises administering to said human or animal subject an effective amount of a compound of formula (I) as defined in claim 1 or a physiologically acceptable solvate thereof.

* * * * *